(12) United States Patent
Kim et al.

(10) Patent No.: US 7,084,969 B2
(45) Date of Patent: Aug. 1, 2006

(54) METHOD OF OPTIMIZING FOCUS OF OPTICAL INSPECTION APPARATUS AND METHOD AND APPARATUS OF DETECTING DEFECTS USING THE SAME

(75) Inventors: Deok-Yong Kim, Gyeonggi-do (KR); Seong-Jin Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 328 days.

(21) Appl. No.: 10/801,525

(22) Filed: Mar. 12, 2004

(65) Prior Publication Data

US 2004/0178351 A1     Sep. 16, 2004

(30) Foreign Application Priority Data

Mar. 14, 2003   (KR) ..................... 10-2003-0016144

(51) Int. Cl.
*G01N 21/00* (2006.01)

(52) U.S. Cl. .............................. 356/237.4; 356/237.5; 250/559.45; 382/149

(58) Field of Classification Search .. 356/237.1–237.5, 356/394; 250/201.4, 559.45; 369/44.27, 369/44.34; 382/149
See application file for complete search history.

(56) References Cited

U.S. PATENT DOCUMENTS 6,298,019 B1 * 10/2001 Watanabe et al. ........ 369/44.27
6,338,926 B1    1/2002 Ku et al.
6,696,679 B1 *  2/2004 Graef et al. ............. 250/201.4
2004/0141640 A1 * 7/2004 Lee et al. .................. 382/149
2004/0150813 A1 * 8/2004 Kim et al. ............... 356/237.1

FOREIGN PATENT DOCUMENTS

| JP | 6-281409 | 10/1994 |
| KR | 1999-023205 | 3/1999 |
| KR | 1999-0072263 | 9/1999 |

OTHER PUBLICATIONS

English language abstract of Japanese Publication No. 6-281409.
English language abstract of Korean Publication No. 1999-0072263.
English language abstract of Korean Publication No. 1999-023205.

* cited by examiner

*Primary Examiner*—Hoa Q. Pham
(74) *Attorney, Agent, or Firm*—Marger Johnson & McCollom, P.C.

(57) ABSTRACT

According to a method of optimizing a focus of an optical inspection apparatus, a first light is irradiated onto a substrate. Then, the first light is reflected on the substrate to form a second light. The second light is sensed with various foci to form image information corresponding to each of the foci. Then, a relation between foci of the optical inspection apparatus and gain value corresponding to the image information is obtained. Then, the focus corresponding to a minimum gain value is set up as an optimized focus. Thus, a focus of an optical inspection apparatus is accurately adjusted to enhance efficiency of defecting defects, so that defects of semiconductor apparatus are more accurately detected.

24 Claims, 8 Drawing Sheets

METHOD OF OPTIMIZING FOCUS OF OPTICAL INSPECTION APPARATUS AND METHOD AND APPARATUS OF DETECTING DEFECTS USING THE SAME

CROSS-REFERENCE TO RELATED APPLICATIONS

This application relies for priority upon Korean Patent Application No. 2003-16144, filed on Mar. 14, 2003, the contents of which are herein incorporated by reference in their entirety.

BACKGROUND OF THE INVENTION

1. Field of the Invention

This disclosure relates to optical inspection methods and apparatus, and in particular, to a method of optimizing a focus of an optical inspection apparatus having enhanced efficiency of detecting detects and a method and an apparatus of detecting defects using the focus optimizing method.

2. Description of the Related Art

Semiconductor devices are manufactured via various manufacturing processes, for example, using processes such as doping, diffusion, thermal oxidation, chemical vapor deposition, etching, exposure, etc. The above-mentioned processes are performed in sequence on a wafer or glass by process apparatuses.

When a manufacturing process is performed, the wafer or glass is examined for generated defects. As the wafer becomes larger, the time required for the examining process increases. Thus, manufacturing costs increase as well.

In order to examine defects of the wafer, a scanning electron microscope (SEM) is widely used. In a method of detecting defects by using the SEM, an electron beam is scanned on a wafer, and secondary electrons from the wafer are detected, so that the second electrons are converted into an image signal for detecting defects.

However, this method of detecting defects by using the SEM requires much time and cost. Furthermore, automation of the method is not possible.

Additionally, various methods of detecting defects or monitoring the manufacturing process have been disclosed. For example, Japan laid open publication number 1994-281409 discloses a method and apparatus of detecting defects. That is, when detecting defects of a wafer having multiple layers, each layer is focused independently to detect defects of the layer.

U.S. Pat. No. 6,338,926 discloses a method for easily finding an optimized focus. According to the method, a specially designed pattern is used for focusing. Korean laid open publication number 1999-72263 discloses a monitoring method and a monitoring apparatus. According to the method and the apparatus, a resolving power and focusing of the apparatus are monitored during the manufacturing processes, so that the focus data points are optimized.

Korean laid open publication number 1999-23205 discloses a conditional monitoring method of lithography and etching process, which provides an evaluating method for focus exposure and etching parameters.

However, none of the methods or apparatus described above teach or disclose a method of detecting defects by a relation between the focus and the defect detecting efficiency of an optical inspection apparatus. For example, when using an SEM electron beam, although many researches have been performed, however, in case of an optical inspection apparatus, no research about focusing, which is one of the factors related to defect detecting efficiency, has yet been systematically performed.

Thus, for conventional optical inspection apparatus, even for different layered films, the same focus is used, or an operator adjusts the focus according to his own experience. Consequently, the defect detecting efficiency is lowered, the time required to detect defects is greater, and the overall reliability and productivity of a semiconductor device decreases.

SUMMARY OF THE INVENTION

Some embodiments of the invention provide a method of optimizing a focus of an optical inspection apparatus that is capable of enhancing the defect detection efficiency. Other embodiments of the invention provide a method of rapidly detecting defects by employing the focus optimizing method. Still other embodiments provide an apparatus for detecting detects that employs the focus optimizing method.

BRIEF DESCRIPTION OF THE DRAWINGS

The above and other features and advantages of embodiments of the invention will become more apparent by describing in detail exemplary embodiments with reference to the accompanying drawings.

DETAILED DESCRIPTION OF THE INVENTION

Hereinafter, the preferred embodiments of the present invention will be described in detail with reference to the accompanied drawings.

Figure 1:
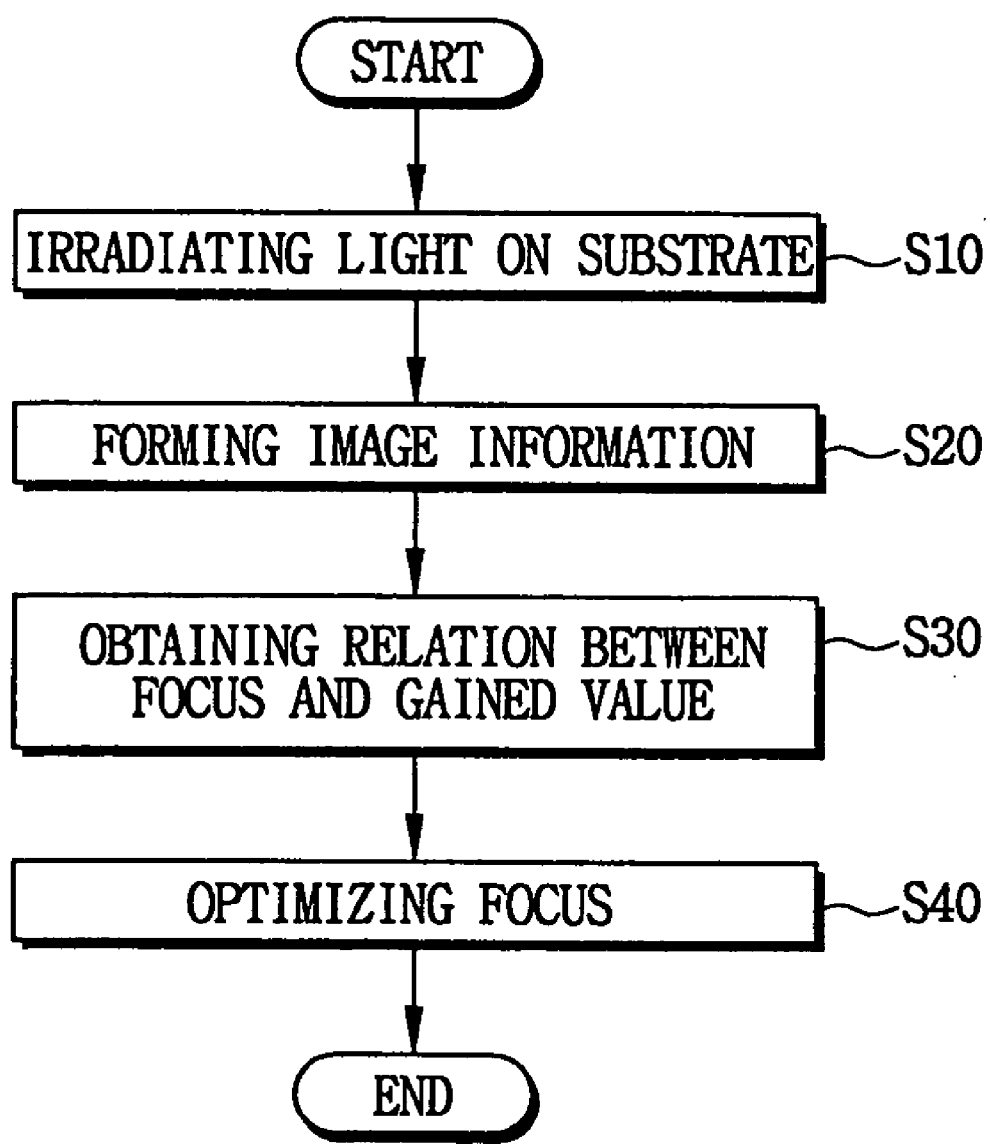
FIG. 1 is a flow chart illustrating a focus optimizing method for an optical inspection apparatus according to some embodiments of the invention.

FIG. 1 is a flow chart illustrating a focus optimizing method for an optical inspection apparatus according to some embodiments of the invention.

Referring to FIG. 1, in process S10, a light is irradiated on a substrate. In the next process S20, image information is formed by sensing a light reflected on the substrate while changing the focus.

In process S30, the relation between the focus and the value gain from an optical inspection apparatus may be obtained.

Later in process S40, the focus of the optical inspection apparatus may be optimized via the relation.

Hereinafter, the focus optimizing method according to some embodiments of the invention will be explained in detail.

In order to optimize a focus of the optical inspection apparatus, a light is irradiated onto a substrate that is to be examined in process S10. The substrate corresponds to a semiconductor wafer that has undergone a manufacturing processes, for example, such as a doping, diffusion, thermal oxidation, chemical vapor deposition, etching, or exposure process, etc. The light is irradiated in a 'light level box' that is virtually defined on the substrate. A light having a short wavelength is preferred so as to reduce refraction and interference. An ultraviolet light, for example, may be irradiated on to the substrate.

Then, a light reflected from the substrate is sensed and converted into the image information under various foci in process S20. Then, various image information corresponding to each of the various foci is generated.

In the optical inspection apparatus, the light sensed is converted into a current that corresponds to an analog signal. The current is converted into a digital image signal using an analog-to-digital (A/D) converter, so that a gray scale level for each pixel corresponding to an area of the substrate is formed. The gray scale level corresponds to an 8 bit digital signal. Thus, the gray scale level has 256 gradations.

Hereinafter, the process of forming the image information will be explained.

Figure 2:
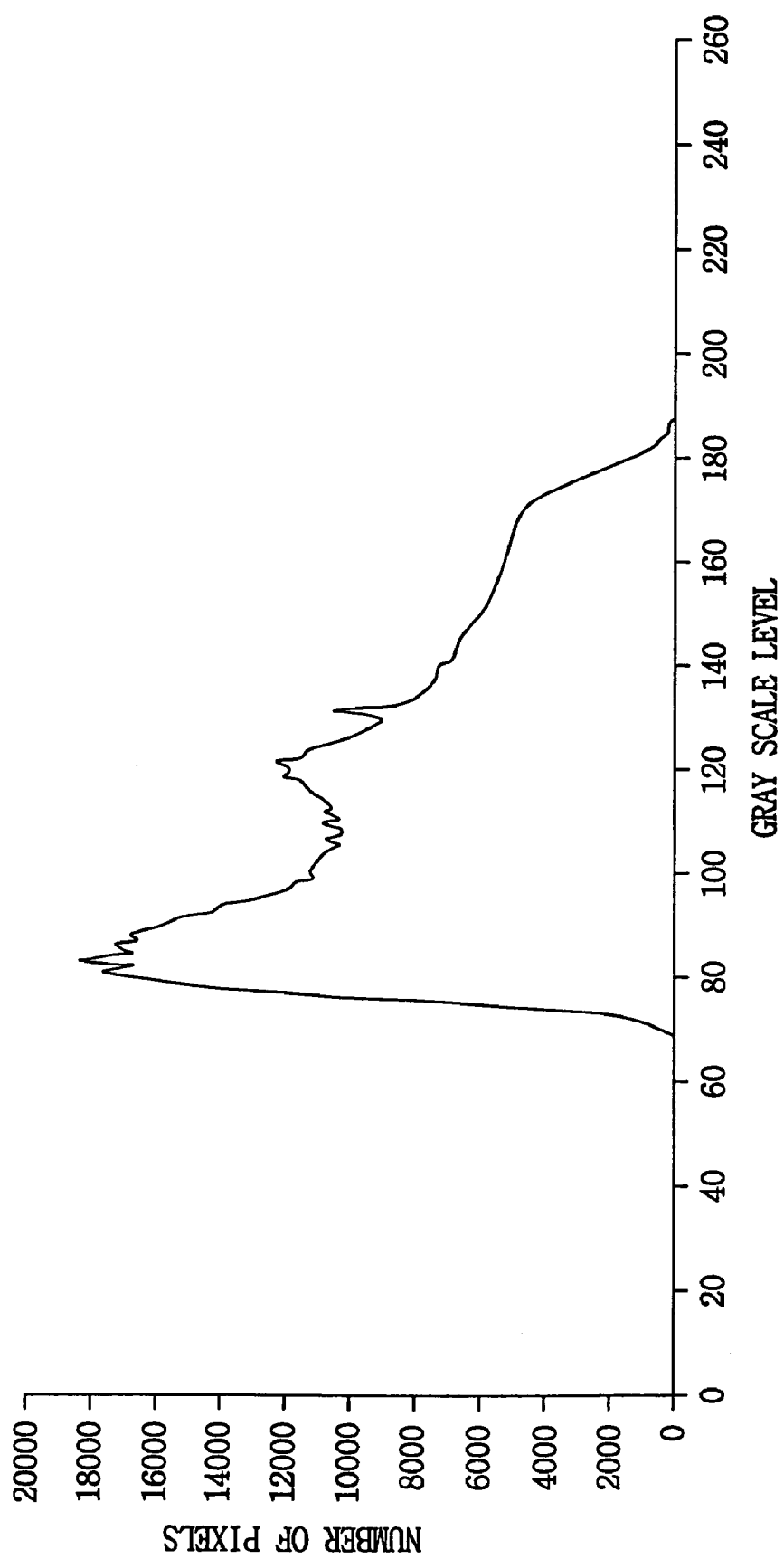
FIG. 2 is a graph illustrating the gray scale level of a light reflected on a semiconductor substrate that has undergone a chemical mechanical polishing (CMP) process.

FIG. 2 is a graph illustrating the gray scale level of a light reflected on a semiconductor substrate that has undergone a chemical mechanical polishing (CMP) process. The semiconductor substrate of FIG. 2 has undergone the CMP process in a shallow trench isolation (STI) process. The graph of FIG. 2 corresponds to an optimum gray level obtained by changing a gain value and an offset value. The gray scale level is set to be in a range from, for example, the 70th level to the 180th level, and an optimum intensity, a gain value, and a offset value are obtained via 'light level training'.

Light level training is a method for optimizing the gray scale level by changing the intensity, the gain value, and the offset value of the optical inspection apparatus. The gray scale level of the optical inspection apparatus may range from 0 to 255. In the optical inspection apparatus, the intensity, the gain value, and the offset value for forming a graph of a gray scale level that optimizes defect detection are automatically set, so that an optimal condition of the optical inspection apparatus may be obtained.

The gain value is a parameter that adjusts the gray scale level for individual pixels. When the gain value is changed from one to two, the difference between the minimum and maximum values of the gray scale level is doubled. For instance, when the gain value is one, the difference between the maximum and minimum of the gray level is 40. If the gain value is changed to two, the difference between the maximum and minimum of the gray scale becomes 80.

The offset value is a parameter that determines a level of the gray scale level, and the gray level graph is positioned between the 0th and 25th gray scale level due to the offset value.

The optimum gray scale level refers to a maximally enlarged gray scale difference between a maximum gray scale level of a pixel and a minimum gray scale level of another another pixel. As the difference between the maximum gray scale level and the minimum gray scale level becomes larger, the defect detection efficiency increases. In light level training, when the intensity of a light increases or the offset value decreases, the gray scale level of the pixel increases.

Using the parameters define above, a relationship between the various foci of the optical inspection apparatus and the gain values corresponding to the foci may be obtained.

A reason for obtaining this relationship will be explained below with reference to FIGS. 3 to 6.

Figure 3:
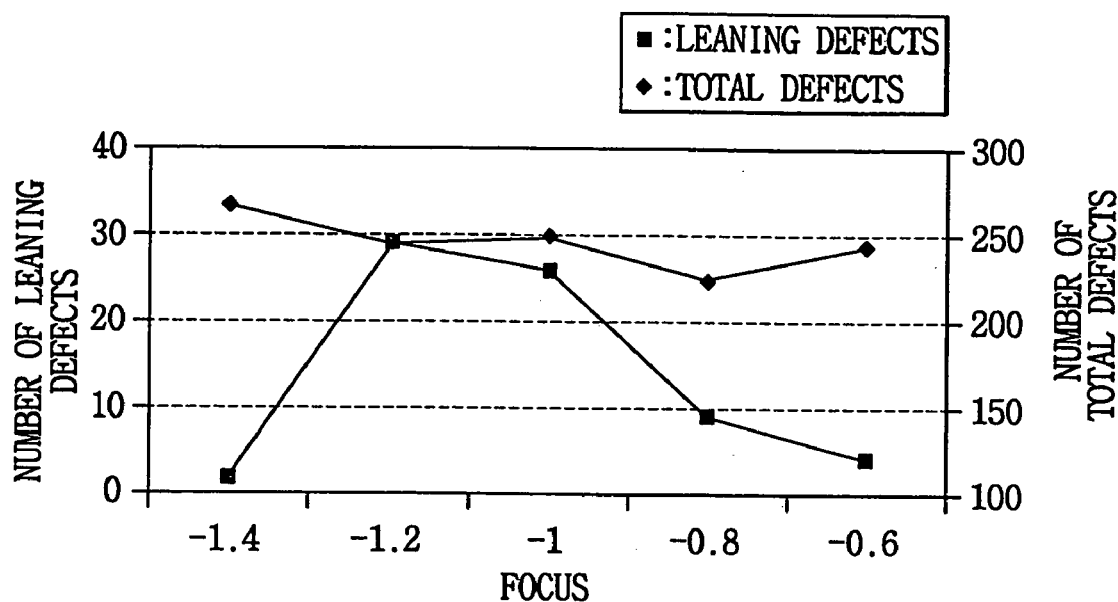
FIG. 3 is a graph illustrating the relation between the number of leaning defects, the focus, and the total number of defects for an example polysilicon film.

FIG. 3 is a graph illustrating the relationship between the number of leaning defects, the focus, and the total number of defects in the case of a polysilicon film.

FIG. 3 illustrates that the detection efficiency for leaning defects changes in accordance with the focus. The leaning defects correspond to contacts between adjoining patterns of the semiconductor substrate. As design rules becomes smaller or the degree of integration of semiconductor devices increase, leaning defects will occur more frequently.

When the focus is in a range from about −1.4 to about −0.6, the variance between the total number of detected defects is relatively small. That is, the total number of defects ranges from about 224 to about 267. However, the number of leaning defects detected changes greatly over the same range of focus. The maximum number of leaning defects are detected when the focus is in a range from about −1.2 to about −1.0. Thus, the detection efficiency for leaning defects is maximized when the focus of the optical inspection apparatus ranges from about −1.2 to about −1.0, therefore it is preferable to set the focus in that range.

Figure 4:
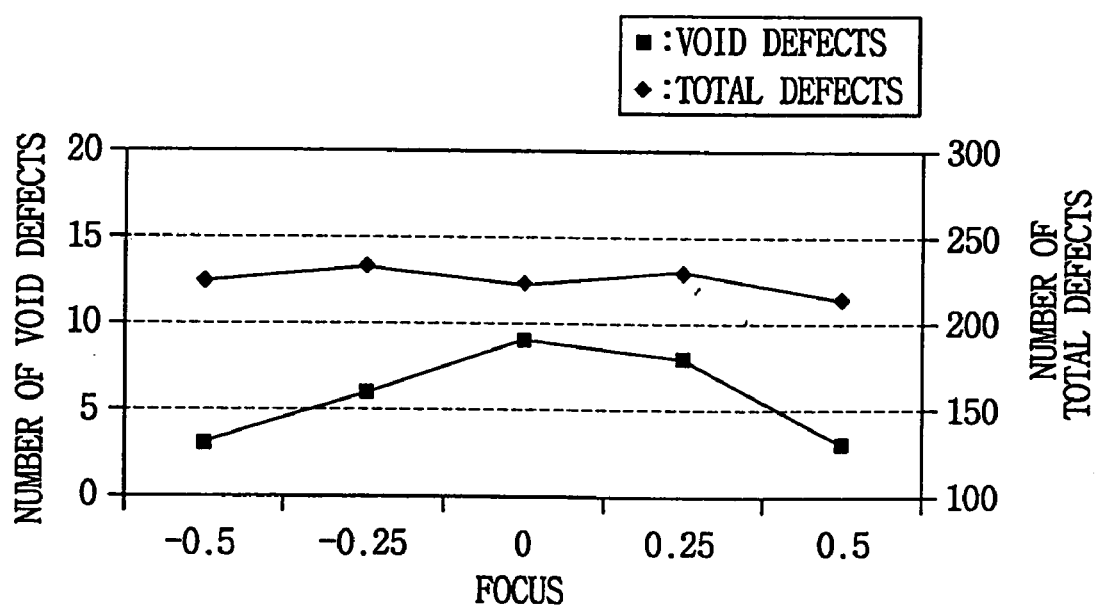
FIG. 4 is a graph illustrating the relation between the number of leaning defects, the focus, and the total number of defects when the semiconductor substrate has undergone a chemical mechanical polishing process.

FIG. 4 is a graph illustrating the relationship between the number of detected leaning defects, the focus, and the total number of detected defects after the semiconductor substrate has undergone a CMP process.

After a STI-CMP process, the detection of void defects is of significant importance. FIG. 4, illustrates that the void defect detection changes appreciably in accordance with the focus. When the focus is in a range from about −0.5 to about 0.5, the total number of detects does not vary much. However, the number of detected void defects is much greater when the focus is in a range from about 0 to 0.25. Thus, the the focus is preferably set in a range from about 0 to about 0.25 to maximize the void defect detection efficiency.

For conventional optical inspection apparatus, the effect of the focus on the defect detection efficiency has not been considered. That is, substantially the same focus is used for detecting defects on each layer of a multilayer semiconductor substrate, or the focus is subjectively adjusted by an operator based on his experience.

According to the above-described experimental results, however, the focus has an influence on the defect detection efficiency.

Figure 5:
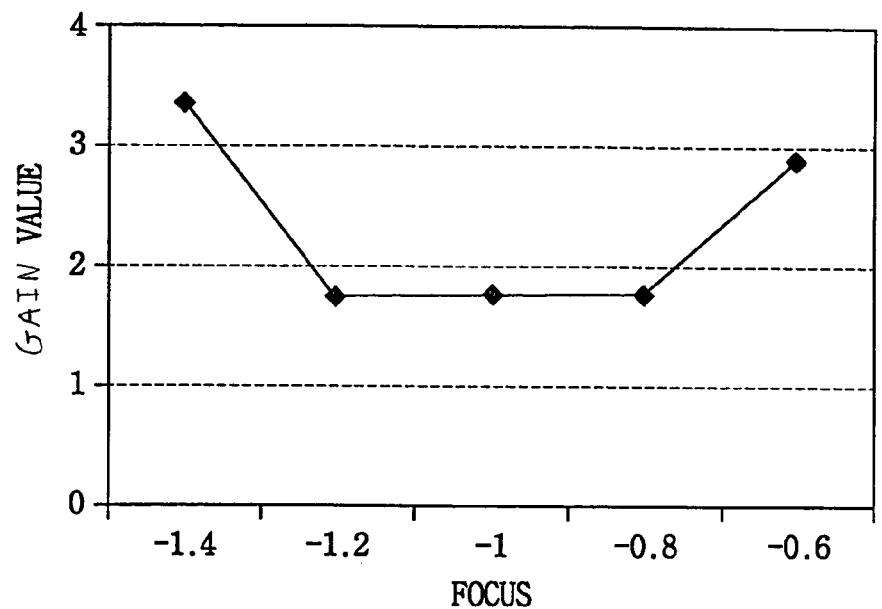
FIG. 5 is a graph illustrating the relation between the focus and a value gain from an optical inspection apparatus in the case of a polysilicon film.

FIG. 5 is a graph illustrating the relation between the focus and the gain value for an optical inspection apparatus when the apparatus is illuminating a polysilicon film.

Referring to FIG. 5, for an arbitrary light intensity and offset value, the gain value changes in accordance with the focus when light level training is performed on the polysilicon film. According to FIG. 5, a minimum gain value is obtained when the focus is about −1.2.

Figure 6:
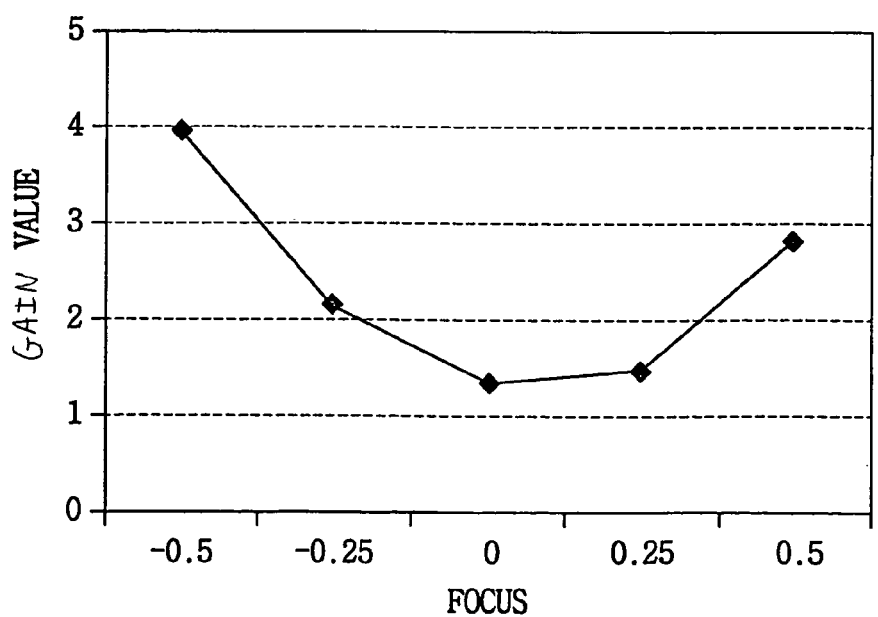
FIG. 6 is a graph illustrating the relation between a focus and the value gain from an optical inspection apparatus in the case of a semiconductor substrate that has undergone a chemical mechanical polishing process.

FIG. 6 is a graph illustrating the relation between the focus and the gain value from an optical inspection apparatus when the apparatus is illuminating a semiconductor substrate that has undergone a CMP process.

Referring to FIG. 6, for an arbitrary light intensity and offset value, the gain value changes in accordance with the focus when light level training is performed on the semiconductor substrate that has undergone a CMP process. According to FIG. 6, a minimum gain value is obtained when the focus is about 0.

According to the results described above, both the defect detection efficiency and the gain value are related to the focus of the optical inspection apparatus. Thus, when the defect detection efficiency and the gain value vary in a significant trend, the optimum focus may be determined by the gain value.

Thus, the focus corresponding to the minimum gain value is selected as the optimum focus for the optical inspection apparatus.

Figure 7:
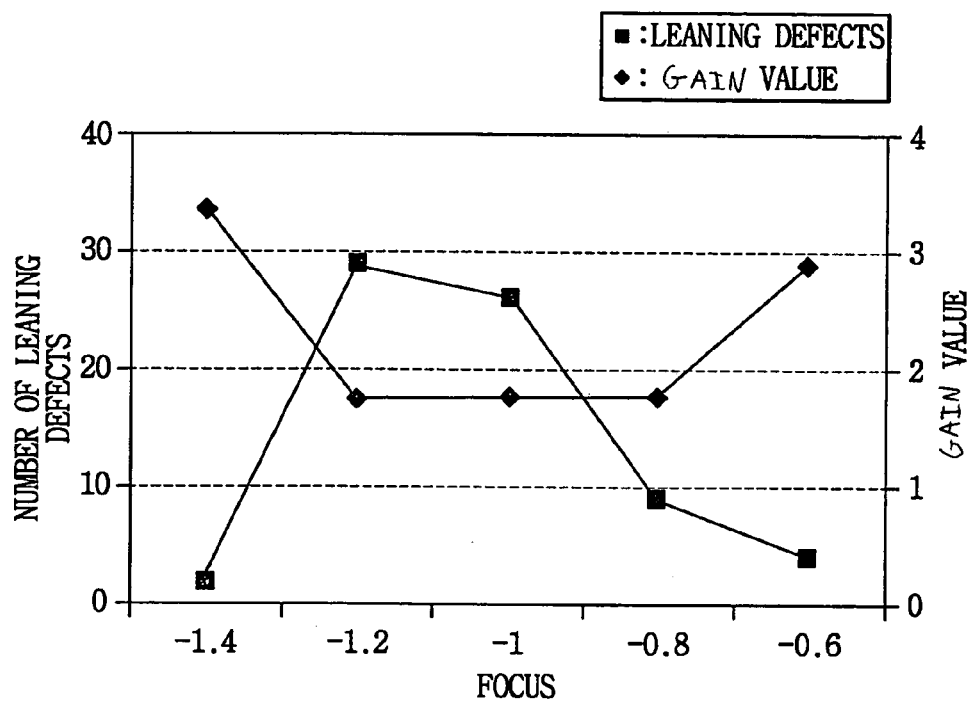
FIG. 7 is a graph illustrating the relation between the number of leaning defects, the focus, and the gain value in the case of a polysilicon film.

FIG. 7 is a graph illustrating the relation between the number of detected leaning defects, the focus, and the gain value when the optical inspection apparatus is illuminating a polysilicon film.

Referring to FIG. 7, for an arbitrary intensity and offset value, a relationship between the gain value and the number of leaning defects detected in the polysilicon film may be obtained from the light level training. FIG. 7 illustrates that when the focus is about −1.2, the gain value is the lowest and the number of detected leaning defects is maximized. As the gain value increases, the number of detected leaning defects decreases.

Figure 8:
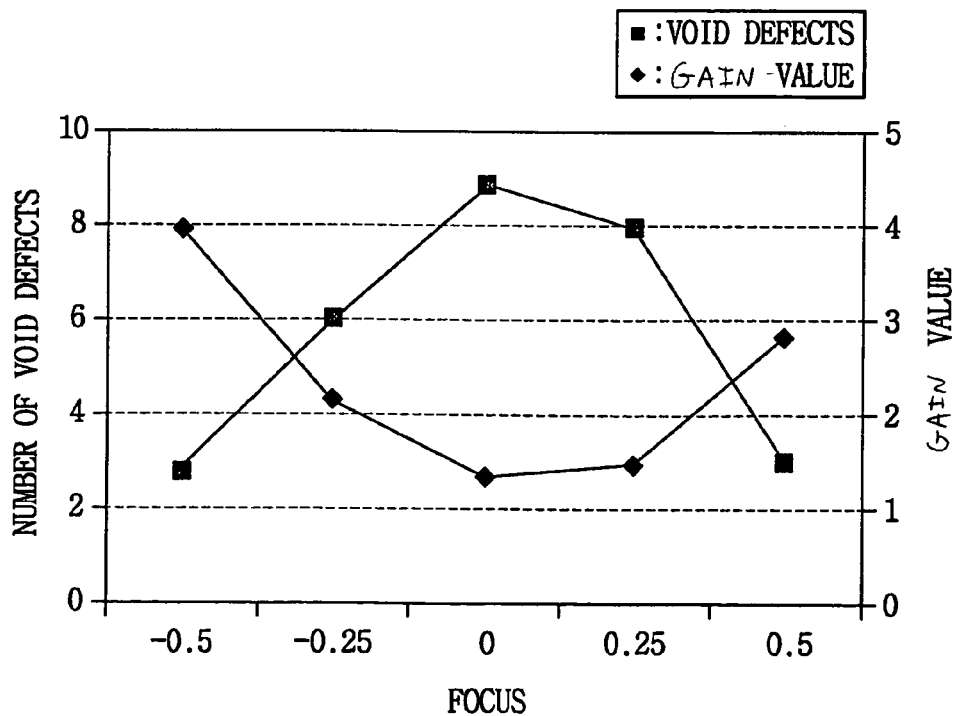
FIG. 8 is a graph illustrating the relation between the number of void defects, the focus, and the gain value in the case of a semiconductor substrate that has undergone a chemical mechanical polishing process.

FIG. 8 is a graph illustrating the relation between the number of detected void defects, the focus, and the gain value when the optical inspection apparatus is illuminating a semiconductor substrate that has undergone a CMP process.

Referring to FIG. 8, for an arbitrary intensity and offset value, a relationship between the gain value and the number of void defects detected in a layer that has undergone STI-CMP may be obtained from the light level training. Specifically, when the focus is about 0, the gain value is the lowest and the number of detected void defects is maximized. As the gain value increases, the number of void defects decreases.

As explained above, the focus of the optical inspection apparatus influences the defect detection efficiency, and the defect detection efficiency is maximized when the gain value obtained from the light level training is the lowest. Thus, when a focus corresponding to the lowest gain value is set on the optical inspection apparatus, the defect detection efficiency is maximized. The gain value may be obtained in about a minute for a particular focus setting. Thus, obtaining the optimum focus becomes a simple and relatively quick process.

Hereinafter, a method of rapidly detecting defects of a semiconductor substrate by using the optical inspection apparatus with optimum focus will be explained.

Figure 9:
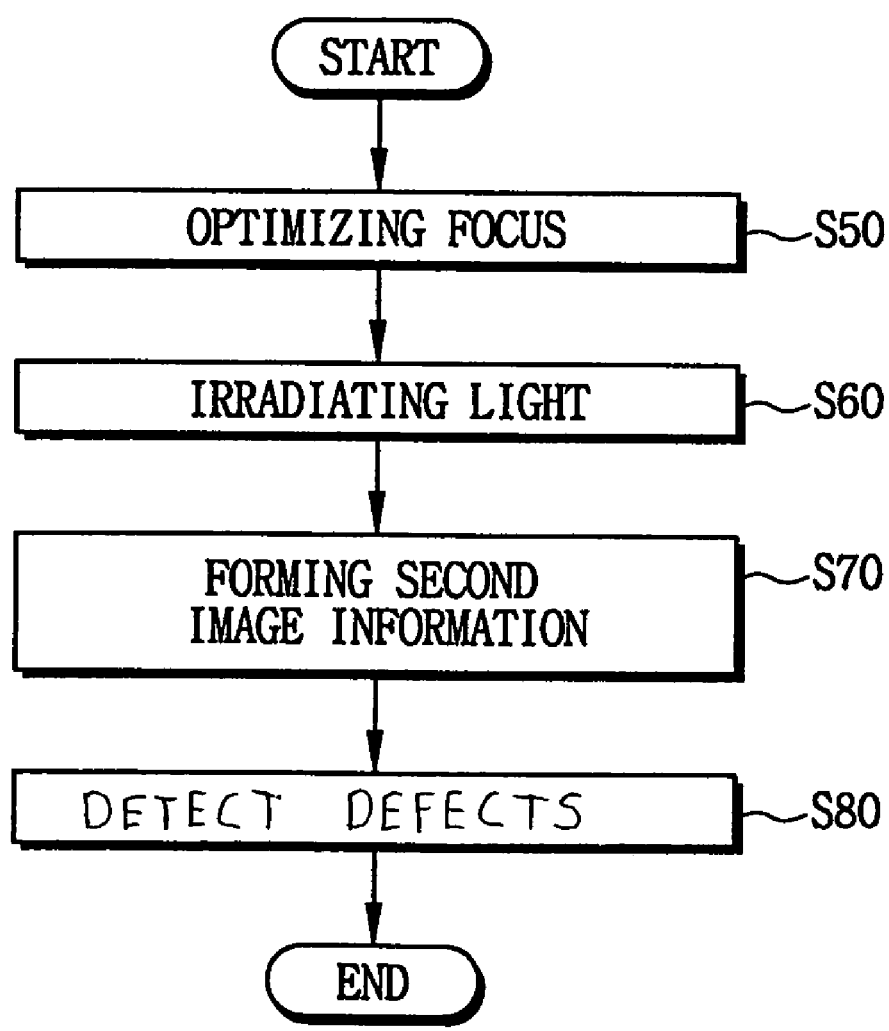
FIG. 9 is a flow chart illustrating a method of detecting defects by optical method according to other embodiments of the invention.

FIG. 9 is a flow chart illustrating a method of detecting defects by optical method according to some embodiments of the invention.

Referring to FIG. 9, in process S50, a focus of the optical inspection apparatus is set to the optimum value using the principles explained above. Then, in process S60, a light is irradiated onto an objective semiconductor substrate. In process S70, the light reflected from the objective semiconductor substrate is sensed to form secondary image information. Subsequently, in process S80, it is determined whether or not the objective semiconductor substrate is defective.

Hereinafter, the method of detecting defects on the semiconductor substrate will be explained in detail.

A first light is irradiated onto the objective semiconductor substrate and a plurality of identical patterns is formed thereon.

Then, a first reflected light is sensed for a particular focus setting to form first image information.

Furthermore, when the first reflected light is sensed, a current corresponding to an analog signal is generated according to the intensity of the first reflected light. Later, the current is converted into a digital image signal by an A/D converter to form pixels, each pixel having a gray scale level. Each pixel is associated with a corresponding area of the semiconductor substrate.

The gray scale level is converted into an 8 bit digital signal, so that the gray scale level is divided into 256 levels.

A relationship between the foci of the optical inspection apparatus and the gain values corresponding to the first image signal formed from each of the foci is obtained. Both the defect detection efficiency and the gain value have a relationship to the focus of the optical inspection apparatus. Therefore, when the defect detection efficiency and the gain value vary in a certain pattern, the optimum focus may be determined by the gain value that maximized defect detection efficiency.

The focus of the optical inspection apparatus is then set to the optimum value as described above in process S50. The focus of the optical inspection apparatus influences the defect detection efficiency. That is, when the gain value obtained by the light level training is minimal, the defect detection efficiency is greatest. Thus, when the focus corresponding to the minimum gain value is set, the defect detection efficiency is maximized.

A second light is irradiated onto the objective semiconductor substrate in process S60.

The second light is a light having a relatively short wavelength, for example, ultraviolet light, so that refraction and interference effects are reduced.

The second light that is reflected from the objective semiconductor substrate is sensed with the optical inspection apparatus having the optimum focus to form the second image information in process S70, similar to the formation of the first image information.

Process S80 determines whether or not the objective semiconductor substrate is defective. When the objective semiconductor substrate is checked for a defect, a threshold value may be used. That is, image information of an objective pixel is subtracted from image information of a pixel adjacent to the objective pixel to form primitive data. When an absolute value of the primitive data is larger than the threshold value, the area of the semiconductor corresponding to the objective pixel is determined to be defective.

Figure 10:
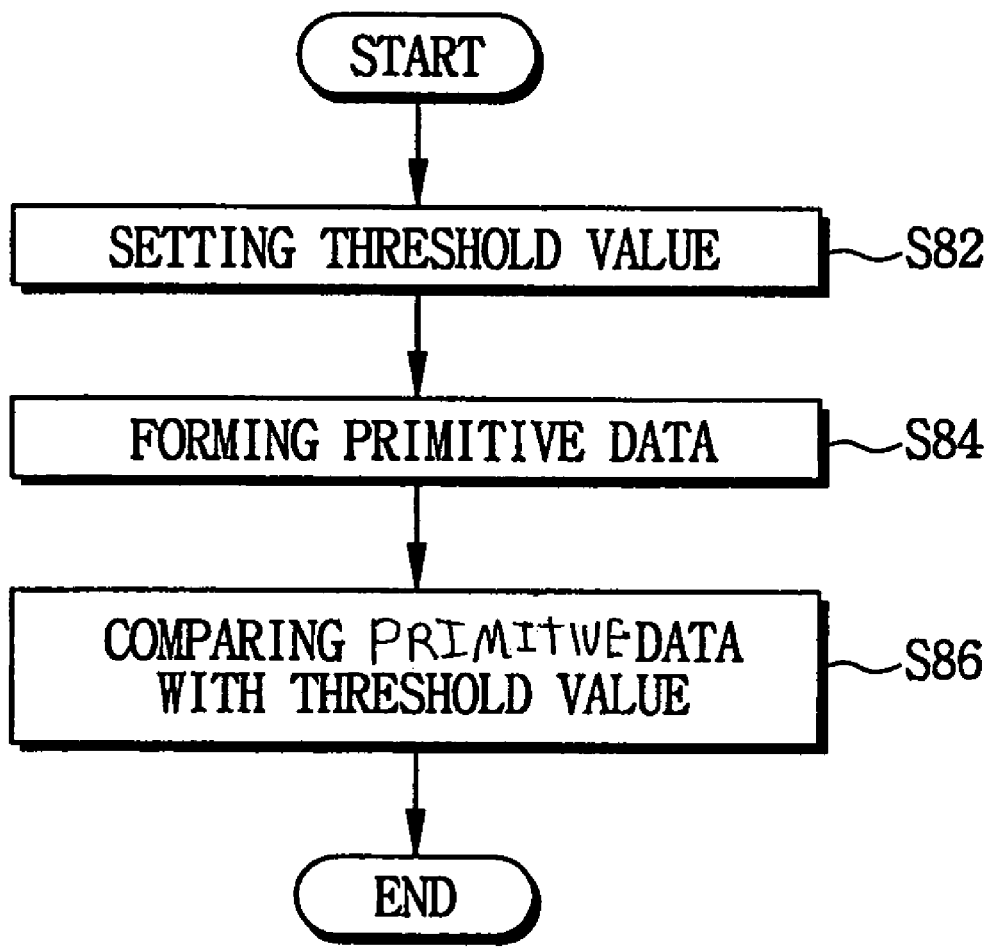
FIG. 10 is a flow chart illustrating a method of determining detects according to some other embodiments of the invention.

FIG. 10 is a flow chart illustrating a method of determining detects according to some embodiments of the invention.

Referring to FIG. 10, the threshold value is first set in process S82. Further, image information of an objective pixel is subtracted from image information of a pixel adjacent to the objective pixel to form primitive data in process S84. When the primitive data is a negative value, the primitive data is converted into a positive value by taking an absolute value.

In process S86, the primitive data is compared with the threshold value. If the primitive data is larger than the threshold value, the area of the semiconductor substrate corresponding to the objective pixel is determined to be defective.

Embodiments of the invention are not limited to the above-explained method. That is, various methods may be used as far as the focus is optimized according to the present invention.

Hereinafter, an apparatus for detecting defects will be explained.

Figure 11:
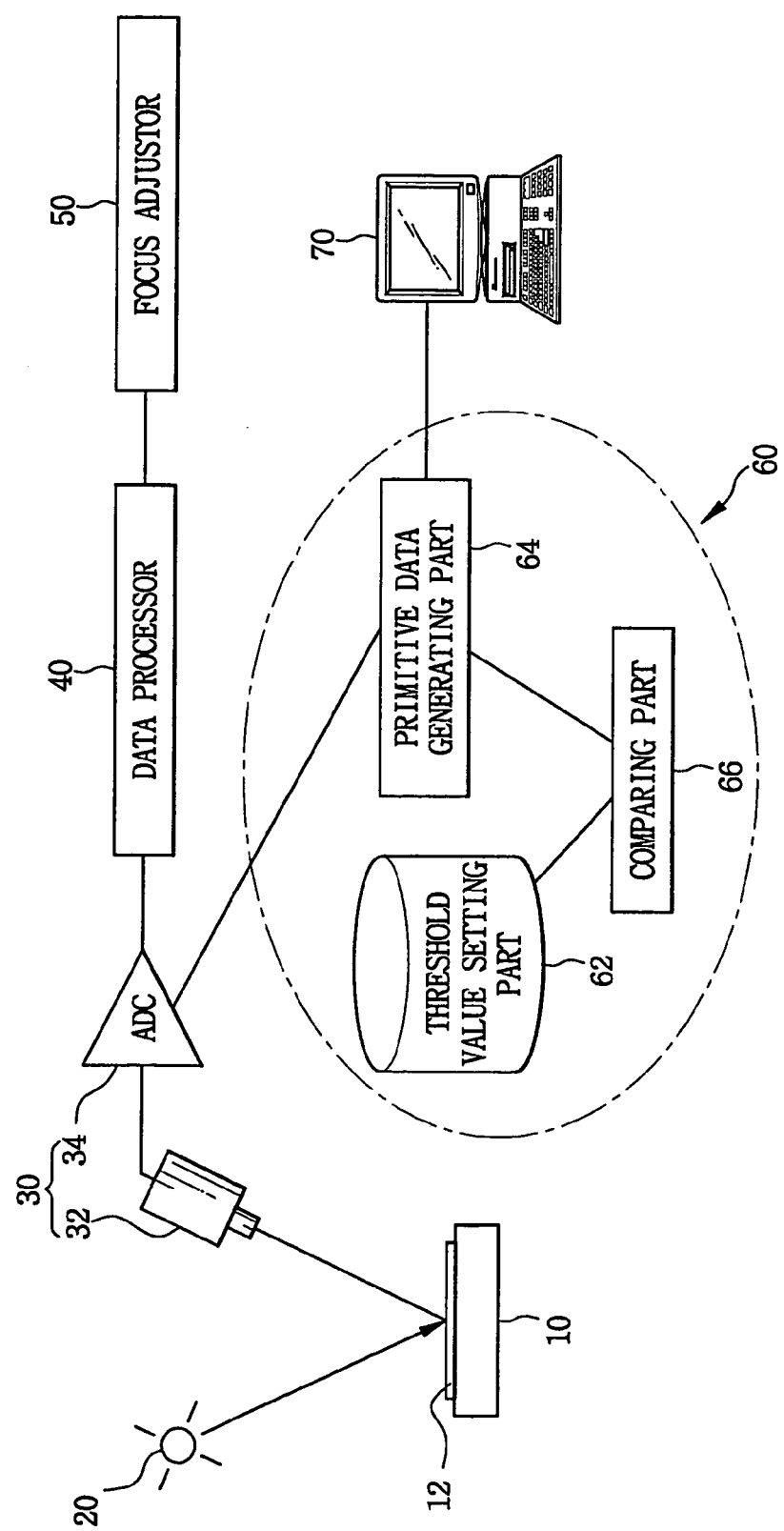
FIG. 11 is a block diagram illustrating an apparatus for detecting defects according to some embodiments of the invention.

FIG. 11 is a block diagram illustrating an apparatus for detecting defects.

Referring to FIG. 11, an exemplary apparatus for detecting defects includes a supporting plate 10, a light source 20, an image information generator 30, a data processor 40, a focus adjustor 50, and a defect detector 60. The supporting plate 10 supports a substrate 12. The light source 20 irradiates a light onto the substrate 12. The image information generator 30 senses a light reflected from the substrate 12 to generate image information that contains a gain value. The data processor 40 analyzes the relation between the gain value of the image information and the focus. The focus adjustor 50 adjusts the focus. The defect detector 60 detects a pixel that indicates a corresponding defective area of the substrate by using the analyzed relation between the gain value of the image information and the focus.

When the substrate 12 has undergone a manufacturing process, for example, such as CMP, etc., the substrate 12 is transferred to the supporting plate 10, and the substrate 12 is disposed on the supporting plate 10. The substrate 12 includes a number of unit devices having patterns. The patterns of the unit devices are represented by pixels in the image information generator 30. When the substrate 12 corresponds to a semiconductor substrate, the unit device corresponds to a cell that forms a circuit device. The substrate 12 is loaded or unloaded by a general wafer loading mechanism, for example, such as a robot arm.

The apparatus for detecting defects includes the light source 20 that generates a light to irradiate onto the substrate 12. The light, for example, such as ultraviolet light, has short wavelength, so as to reduce refraction and interference.

The image information generator 30 generates the image information by a light reflected from the substrate 12. The image information generator 30 senses the light to form image information, each pixel of the image information having a gain value parameter.

In detail, the image information generator 30 includes an image detector 32 and an analog-to-digital converter 34. The image detector 32 detects the light reflected from the substrate 12 to generate an analog image signal from the light. The analog-to-digital converter 34 converts the analog image signal into a digital image signal.

The data processor 40 analyzes a relation between the gain value of the image information and the focus. As described above, the focus influences the defect detection efficiency, and the gain value also influences the defect detection efficiency. Thus, the data processor 40 analyzes the relation between the gain value and the focus to optimize the focus.

The focus adjustor 50 adjusts the focus. That is, the focus adjustor 50 adjusts the focus so that it corresponds to a minimum gain value. As described above, when the focus corresponds to the minimum gain value, the defect detection efficiency is maximized.

The defect detector 60 detects pixels that correspond to defective areas of the substrate with the analyzed relation between the gain value of the image information and the focus. The defect detector 60 includes a threshold value setting part 62, a primitive data generating part 64 and a comparing part 66. The threshold value setting part 62 sets up the threshold value. The primitive data generating part 64 subtracts image information of an objective pixel from image information of a pixel adjacent to the objective pixel to form primitive data. The comparator compares the threshold value with an absolute value of the primitive data to determine whether or not the objective pixel indicates a defective area of the substrate.

The apparatus for detecting defects may further include a monitor 70 for displaying pixels corresponding to defects and the primitive data of the pixels.

The apparatus for detecting defects according to the above embodiments of the invention detects defects rapidly and accurately, so that reliability of a semiconductor is increased.

According to embodiments of the invention, a focus of an optical inspection apparatus is accurately adjusted to enhance defect detection efficiency, so that defects in semiconductor devices are more accurately detected. Thus, the reliability of semiconductor devices is enhanced. Further, the manufacturing time and cost are reduced, thereby increasing productivity.

Embodiments of the invention may be practiced in many ways. What follows are exemplary, non-limiting descriptions of some embodiments of the invention.

According to some embodiments of the invention, a first light is irradiated onto a substrate. Then, the first light is reflected on the substrate to form a second light. The second light is sensed with various foci to form image information corresponding to each of the foci. Then, a relation between foci of the optical inspection apparatus and the gain value corresponding to the image information is obtained. The focus corresponding to a minimum gain value is set up as an optimized focus.

In a method of detecting defects according to some other embodiments of the invention, a first light is irradiated onto a substrate that includes a plurality of unit devices that have patterns. Then, the first light is reflected on the substrate to form a second light. The second light is sensed with various foci to form first image information corresponding to each of the foci. Then, a relation between foci of the optical inspection apparatus and gain value corresponding to the image information is obtained. The focus corresponding to a minimum gain value is set up as an optimized focus. A third light is irradiated onto the substrate, and the third light is reflected from the substrate to form a fourth light. The fourth light is sensed with the optimized focus to form second image information. Defective portions of the substrate are determined using the first and second information.

An apparatus for detecting defects according to still other embodiments of the invention include a supporting plate, a light source, an image information generator, a data processor, a focus adjustor, and a defect detector. The supporting plate supports a substrate that includes a plurality of a unit devices that have patterns. The light source generates a first light irradiated onto the substrate. Then, the first light is reflected from the substrate to form a second light. The image information generator senses the second light to generate image information that includes pixels, each pixel having a gain value. The data processor analyzes a relation between the gain value of the image information and a focus corresponding to the image information. The focus adjustor adjusts focus corresponding to a minimum gain value as an optimized focus. The defect detector detects pixels that indicate defective areas of the substrate using the image information.

According to embodiments of the invention, a focus of an optical inspection apparatus is accurately and rapidly adjusted to enhance the defect detection efficiency, so that defects of semiconductor apparatus are more accurately and rapidly detected. Thus, the reliability of the semiconductor device is enhanced. Furthermore, manufacturing time and cost is reduced, increasing productivity.

Having described some exemplary embodiments of the invention and some attendant advantages, it should be recognized that various changes, substitutions, and alterations can be made without departing from the spirit and scope of the invention as defined by appended claims.

We claim:

1. A method of optimizing a focus of an optical inspection apparatus, comprising:
   irradiating a substrate with a first light;
   sensing a second light reflected from the substrate using at least two focus values to form image information corresponding to the at least two focus values;
   for each of the at least two focus values, obtaining a gain value for the corresponding image information; and
   detecting defects on the substrate with the focus set to one of the at least two focus values that corresponds to a minimum gain value.

2. The method of claim 1, wherein irradiating the substrate comprises irradiating a semiconductor wafer.

3. The method of claim 1, wherein irradiating the substrate with the first light comprises irradiating the substrate with a first wavelength that is shorter than a wavelength in the visible spectrum.

4. The method of claim 3, wherein irradiating the substrate with the first wavelength comprises irradiating the substrate with an ultraviolet wavelength.

5. The method of claim 1, wherein forming image information comprises converting an analog current signal generated in accordance with an intensity of the first light to a digital signal.

6. The method of claim 5, wherein converting the analog current signal to the digital signal comprises converting the analog current signal to a digital signal that represents a gray scale level.

7. The method of claim 6, wherein the gray scale level has 256 levels.

8. A method of detecting defects, comprising:
   irradiating a substrate with a first light, the substrate including a plurality of unit devices;
   sensing a second light reflected from the substrate with at least two focus values to form first image information corresponding to the at least two focus values;
   obtaining a relation between the at least two focus values and at least two gain values derived from the first image information;
   irradiating the substrate with a third light;
   sensing a fourth light reflected from the substrate with an optimized focus to form second image information, the optimized focus substantially equal to one of the at least two focus values that corresponds to a lesser value of the at least two gain values; and
   detecting defects on the substrate using the second image information.

9. The method of claim 8, wherein irradiating the substrate comprises irradiating a semiconductor wafer.

10. The method of claim 8, wherein irradiating the substrate with the first and third lights comprises irradiating the substrate with a first and a third wavelength, respectively, the first and third wavelengths shorter than a wavelength in the visible spectrum.

11. The method of claim 10, wherein irradiating the substrate with the first and third wavelengths comprises irradiating the substrate with an ultraviolet wavelength.

12. The method of claim 8, wherein forming second image information comprises converting an analog current signal generated in accordance with an intensity of the third light to a digital signal.

13. The method of claim 12, wherein converting the analog current signal to the digital signal comprises converting to a digital signal that represents a gray scale level.

14. The method of claim 13, wherein the gray scale has 256 levels.

15. The method of claim 8, wherein detecting defects comprises:
   setting a threshold value;
   subtracting the second image information of an objective pixel from the second information of a pixel adjacent to the objective pixel to form image information data; and
   comparing the image information data with the threshold value.

16. An apparatus comprising:
   a supporting plate that supports a substrate that includes a plurality of unit devices;
   a light source configured to irradiate the substrate with a first light;
   an image information generator structure to sense a second light reflected from the substrate and to generate image information having a gain value;
   a data processor structured to analyze a relation between the gain value and a focus used to obtain the image information;
   a focus adjustor structured to set an optimized focus to the focus corresponding to a minimum gain value; and
   a detector structured to determine defects using the image information obtained from the optimized focus.

17. The apparatus of claim 16, the image information generator comprising:
   an image detector structured to sense the second light and to generate an analog image signal; and
   an analog-to-digital converter structured to convert the analog image signal into a digital signal.

18. The apparatus of claim 16, the detector comprising:
   a threshold value setting part structured to establish a threshold value;
   a primitive data generating part structured to generate primitive data by subtracting the image information of an objective pixel from the image information of a pixel adjacent to the objective pixel; and
   a comparator structured to compare an absolute value of the primitive data with the threshold value.

19. The apparatus of claim 16, the first light comprising a first wavelength that is shorter than a wavelength from the visible spectrum.

20. The apparatus of claim 19, the first wavelength comprising an ultraviolet wavelength.

21. The apparatus of claim 16, the image information comprising a digital signal.

22. The apparatus of claim 21, wherein the digital signal comprising a gray scale level.

23. The apparatus of claim 22, the gray scale level divided into 256 levels.

24. The apparatus of claim 16, further comprising a monitor that displays a pixel corresponding to a defective area of the substrate and the primitive data for the pixel.

* * * * *